(12) United States Patent
Kirsch et al.

(10) Patent No.: US 9,271,951 B2
(45) Date of Patent: Mar. 1, 2016

(54) LEVOTHYROXINE FORMULATION WITH ACACIA

(71) Applicant: Mylan Inc., Canonsburg, PA (US)

(72) Inventors: John Kirsch, Waynesburg, PA (US); Ramakrishna Nallamothu, Morgantown, WV (US); Baris E. Polat, Morgantown, WV (US)

(73) Assignee: Mylan Inc., Canonsburg, PA (US)

( * ) Notice: Subject to any disclaimer, the term of this patent is extended or adjusted under 35 U.S.C. 154(b) by 0 days.

(21) Appl. No.: 13/723,485

(22) Filed: Dec. 21, 2012

(65) Prior Publication Data

US 2014/0178511 A1 Jun. 26, 2014

(51) Int. Cl.
| | |
|---|---|
| *A61K 31/198* | (2006.01) |
| *A61K 31/235* | (2006.01) |
| *A61K 36/48* | (2006.01) |
| *A61K 9/20* | (2006.01) |

(52) U.S. Cl.
CPC ............... *A61K 31/198* (2013.01); *A61K 9/205* (2013.01); *A61K 9/2013* (2013.01); *A61K 31/235* (2013.01); *A61K 36/48* (2013.01)

(58) Field of Classification Search
None
See application file for complete search history.

(56) References Cited

U.S. PATENT DOCUMENTS

| | | | |
|---|---|---|---|
| 3,090,724 A | 5/1963 | Bowen, Jr. | |
| 6,245,350 B1 | 6/2001 | Amey et al. | |
| 6,569,463 B2 | 5/2003 | Patel et al. | |
| 6,645,526 B2 | 11/2003 | Hanshew, Jr. et al. | |
| 6,936,274 B2 | 8/2005 | Hanshew, Jr. et al. | |
| 7,052,717 B2 * | 5/2006 | Hanshew et al. ............. | 424/464 |
| 7,195,779 B2 | 3/2007 | Hanshew, Jr. et al. | |
| 7,955,621 B2 | 6/2011 | Konieczna et al. | |
| 8,071,134 B2 | 12/2011 | Mousa et al. | |
| 2005/0187607 A1 | 8/2005 | Akhtar et al. | |
| 2008/0058420 A1 | 3/2008 | Rampoldi et al. | |
| 2008/0286343 A1 | 11/2008 | Cengic et al. | |
| 2011/0142941 A1 | 6/2011 | Davis et al. | |
| 2012/0129819 A1 | 5/2012 | Vancaillie et al. | |
| 2014/0179784 A1 | 6/2014 | Kirsch et al. | |

FOREIGN PATENT DOCUMENTS

WO WO 2005/004849 1/2005

OTHER PUBLICATIONS

International Search Report and Written Opinion dated May 28, 2013 for Application No. PCT/US2012/071184.
Shah, R.B., et al., "Stability indicating validated HPLC method for quantification of levothyroxine with eight degradation peaks in the presence of excipients", International Journal of Pharmaceutics, 360 (2008) pp. 77-82.
Collier, J., et al., "Influence of Formulation and Processing Factors on Stability of Levothyroxine Sodium Pentahydrate", AAPS PhannSciTech, vol. 11, No. 2, Jun. 2010.
Patel, H., et al., "The effects of excipients on the stability of levothyroxine sodium pentahydrate tables", International Journal of Pharmaceutics, 264 (2003) 35-43.
Shunichi, N., et al., "The Influence of Cross-Linking Time on the Adsorption Characteristics of Microcapsules Containing Activated Charcoal Prepared by Gelatin-Acacia Coacervation", Chem. Pharm. Bull., 33(11):4649-4656, 1985.

* cited by examiner

*Primary Examiner* — Susan Hoffman
(74) *Attorney, Agent, or Firm* — Frost Brown Todd LLC

(57) ABSTRACT

A pharmaceutical composition comprising thyroxine, acacia, and an antioxidant selected from propyl gallate, butylated hydroxyanisol, and butylated hydroxytoluene is disclosed. The pharmaceutical composition has an improved shelf life. In one embodiment, the composition additionally comprises sucrose, microcrystalline cellulose, and mannitol. The pharmaceutical composition may be used for treating thyroid disorders by orally administering the composition to a patient in need thereof.

20 Claims, No Drawings

LEVOTHYROXINE FORMULATION WITH ACACIA

BACKGROUND

Thyroxine active drugs are known for both therapeutic and prophylactic treatment of thyroid disorders. For example, levothyroxine sodium is prescribed for thyroid hormone replacement therapy in cases of reduced or absent thyroid function in, for example, ailments such as myxedema, cretinism and obesity. See, for example, Post and Warren in *Analytical Profiles of Drug Substances*, Vol. 5, Florey (ed.); Academic Press, New York (1976), pp. 226-281. Levothyroxine sodium is quite unstable, hygroscopic, and degrades rapidly when subjected to high humidity, light, or high temperature. See, for example, Won, *Pharm. Res.* 9(1):131-137, 1992. Because of the chemicophysical properties of the drug, formulations of levothyroxine sodium have extremely short stability duration, which is worsened under conditions of high humidity and temperature. Tablets may decompose approximately 1 percent per month under ambient conditions. Gupta et. al., *J Clin. Pharm. Ther.* 15:331-335, 1990. The stability problem has been so widespread that some drug companies marketing levothyroxine sodium tablets have been forced to recall various batches due to lack of stability.

There have been recent attempts to develop more stable dosage formulations of levothyroxine sodium. For example, U.S. Pat. No. 5,635,209, issued Jun. 3, 1997, to Groenewoud, et al., discloses levothyroxine sodium in combination with potassium iodide as part of a stabilizing excipient. In the manufacture of this formulation, levothyroxine sodium was first mixed with microcrystalline cellulose, and then added to a dried granulation of potassium iodide and microcrystalline cellulose. The formulation purportedly provided increased active drug potency over a three month period in comparison to then commercially available formulations.

In another example, U.S. Pat. No. 5,225,204, issued Jul. 6, 1993, to Chen, et al., discloses a complex of levothyroxine sodium and a cellulose, polyvinylpyrrolidone or Poloxamer. The formulation may be prepared by dissolving the drug complex in a polar organic solvent, adding a cellulose carrier to the liquid, and drying the resulting mixture to obtain a complex of levothyroxine sodium and polyvinylpyrrolidone or Poloxamer adsorbed on the cellulose carrier.

Although purportedly increasing the stability of the formulation, the deposition onto cellulose may have resulted in some increased stability due to improved content uniformity. Tests of such combinations yielded stability results at best equal to commercially available preparations such as those described in U.S. Pat. No. 5,955,105, issued Sep. 21, 1999, to Mitra, et al., and in some cases substantially worse. The inventors of this stabilized composition teach that instability of the dosage form was the result of an interaction between the active drug substance and carbohydrate excipients, and so should be avoided. The inventors also teach that the instability of thyroxine drugs is due to an interaction between the drug and the excipient. These inventors incorporated into the formulation a soluble glucose polymer designed to eliminate the interaction between the drug and other excipients contained in the final blend.

Because of degradation of the active ingredient in currently available formulations of levothyroxine sodium, new methods of formulating solid dosage forms of this drug would be highly desirable. Although different methods for producing a formulation stable enough to meet requirements for shelf-life have been attempted, no method has been entirely successful.

There is, then, a great need for new formulations of thyroxine active drugs with increased stability and shelf life.

BRIEF SUMMARY

A pharmaceutical composition comprising thyroxine, acacia, and an antioxidant selected from propyl gallate, butylated hydroxyanisol, and butylated hydroxytoluene is disclosed. The pharmaceutical composition has an improved shelf life. In one embodiment, the composition additionally comprises sucrose, microcrystalline cellulose, and mannitol.

The pharmaceutical composition may be used for treating thyroid disorders by orally administering the composition to a patient in need thereof.

These and other uses and advantages shall be made apparent from the accompanying drawings and the description thereof.

DETAILED DESCRIPTION

A pharmaceutical composition comprising thyroxine, acacia, and an antioxidant selected from propyl gallate, butylated hydroxyanisol, and butylated hydroxytoluene is disclosed. The pharmaceutical composition has an improved shelf life. Because the shelf life of thyroxine is improved, the dosage of thyroxine is maintained at a predictable level for a longer period of time. In one embodiment, the composition additionally comprises sucrose, microcrystalline cellulose, and mannitol.

Although the description refers to compositions and methods of using thyroxine, the term thyroxine is understood to encompass levothyroxine (L-thyroxine), levothyroxine sodium and other thyroid hormone medications of the general formula:

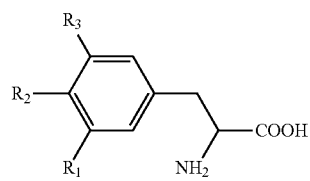

wherein $R_1$ and $R_3$ may be the same or different and are selected from hydrogen; halogen; alkyl; aryl; cycloalkyl; heterocycloalkyl; amide; alcohol; acid; ester; ether; acyl; alkenyl; and alkynyl; wherein $R_2$ is

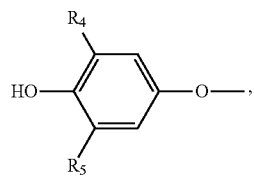

and
wherein $R_4$ and $R_5$ may be the same or different and are selected from hydrogen; halogen; alkyl; aryl; cycloalkyl; heterocycloalkyl; amide; alcohol; acid; ester; ether; acyl; alkenyl; and alkynyl. The thyroxine can be in the form of a free acid, a free base, an organic salt, an inorganic salt, or a hydrate. Liothyronine is an example of a drug encompassed by the above-mentioned general formula.

Formulations of thyroxine with greatly increased resistance to degradation can be produced by providing excipients which reduce or eliminate degradation of the active substance. Although the prior art indicates that reactions between levothyroxine sodium and certain carbohydrate, monosaccharide, or disaccharide excipients is responsible for the poor stability of the drug, the described formulation achieves surprisingly stable thyroxine dosage forms even when these previously disfavored excipients are included. Additionally, in some embodiments, formulations are maintained at a pH of less than about 10.

Stabilized pharmaceutical compositions may be produced by blending thyroxine with acacia and an antioxidant selected from propyl gallate, butylated hydroxyanisol, and butylated hydroxytoluene to form a granulation intermediate. Addition of any additional pharmaceutical excipients, diluents, or granulation aids is optional. Generally, further pharmaceutical excipients may optionally be added to produce final dosage forms such as tablets or capsules.

Acacia is a natural gum also known as gum arabic or gum acacia. It is a mixture of glycoproteins and polysaccharides, and acts as a binder. In one embodiment, the acacia is able to be dissolved in water relatively fast, such as an instant soluble or spray dried grade. In one embodiment, the pharmaceutical composition comprises from about 0.1% to about 10% acacia, from about 0.25% to about 2.5%, from about 0.4% to about 2.0%, or from about 1.0% to about 2.0%.

The pharmaceutical composition comprises an antioxidant selected from propyl gallate, butylated hydroxyanisol, and butylated hydroxytoluene. Antioxidants are compounds which decrease the potential for oxidation, including for example, the oxidation of thyroxine. The pharmaceutical composition may comprise additional antioxidants known to a person of ordinary skill in the art. Propyl gallate is propyl 3,4,5-trihydroxybenzoate. In one embodiment, the pharmaceutical composition comprises from about 0.001% to about 1% propyl gallate, for example, from about 0.005% to about 0.5%, or from about 0.01% to about 0.1%. In one embodiment, the pharmaceutical composition comprises from about 0.001% to about 1% butylated hydroxyanisol, for example, from about 0.005% to about 0.5%, or from about 0.01% to about 0.1%. In one embodiment, the pharmaceutical composition comprises from about 0.001% to about 1% butylated hydroxytoluene, for example, from about 0.005% to about 0.5%, or from about 0.01% to about 0.1%. In one embodiment, the pharmaceutical composition comprises a combination of propyl gallate and butylated hydroxyanisol, or propyl gallate and butylated hydroxytoluene.

In one embodiment, the active ingredient in the composition is levothyroxine sodium. In one embodiment, the pharmaceutical comprises a therapeutically effective amount. The dose will be adjusted to the individual requirements in each particular case. That dosage can vary within wide limits depending upon numerous factors such as the severity of the disease to be treated, the age and general health condition of the patient, other medicaments with which the patient is being treated, any side effects, and the preferences and experience of the medical practitioner involved. A therapeutically effective dosage amount for thyroxine generally ranges from about 0.1 µg to about 5000 µg, such as from about 25 µg to about 300 µg. Exemplary dosages therefore include, but are not limited to 20 µg, 25 µg, 50 µg, 75 µg, 88 µg, 100 µg, 112 µg, 125 µg, 137 µg, 150 µg, 175 µg, 200 µg, and 300 µg. In one embodiment, the solid dosage forms contain the following compounds: levothyroxine sodium (active drug substance); mannitol; microcrystalline cellulose (diluent); sucrose; a disintegrant (such as crospovidone or croscarmellose sodium); propyl gallate; magnesium stearate (lubricant); and colloidal silicon dioxide (glidant). In another embodiment, the solid dosage forms contain the following compounds: levothyroxine sodium (active drug substance); mannitol; microcrystalline cellulose (diluent); sucrose; a disintegrant (such as crospovidone or croscarmellose sodium); butylated hydroxyanisol; magnesium stearate (lubricant); and colloidal silicon dioxide (glidant). In another embodiment, the solid dosage forms contain the following compounds: levothyroxine sodium (active drug substance); mannitol; microcrystalline cellulose (diluent); sucrose; a disintegrant (such as crospovidone or croscarmellose sodium); propyl gallate and butylated hydroxyanisol;

magnesium stearate (lubricant); and colloidal silicon dioxide (glidant). In another embodiment, the solid dosage forms contain the following compounds: levothyroxine sodium (active drug substance); mannitol; microcrystalline cellulose (diluent); sucrose; a disintegrant (such as crospovidone or croscarmellose sodium); butylated hydroxytoluene; magnesium stearate (lubricant); and colloidal silicon dioxide (glidant).

In one embodiment, the composition comprises about 0.1 µg to about 5000 µg thyroxine, such as about 1 µg to about 1000 µg, about 25 µg to about 300 µg. In one embodiment, alditols comprise from about 5% to about 90% (by weight) of the final composition, such as about 15% to about 80%, or about 20% to about 70%. In one embodiment, the alditol is mannitol. In one embodiment, filler, such as carbohydrates (starch or cellulose polymer) and microcrystalline cellulose, comprises about 5% to about 90%, such as about 15% to about 80%, or about 25% to about 70%, by weight of the final formulations. In one embodiment, the final dosage forms comprises about 5% to about 70%, such as about 10% to about 60%, about 15% to about 50%, or about 15% to about 40% saccharide, by weight. In one embodiment, the saccharide is sucrose. Further optional ingredients in the final dosage form may include a disintegrant, which if present, generally forms about 2% to about 30%, such as about 2% to about 15%, or about 3% to about 10% of the final formulation by weight. In one embodiment, lubricants are present in the final composition formulation at about 0.1% to about 5%, such as about 0.2% to about 3%, or about 0.5% to about 2.5% by weight. In one embodiment, glidants are present in the final composition at about 0.05% to about 2%, such as about 0.075% to about 1%, or about 0.1% to about 0.5% by weight. In one embodiment, surfactants are present in the final composition at about 0.005% to about 1%, such as about 0.01% to about 0.5%, or about 0.01% to about 0.2% by weight. In one embodiment, binders are present in the final composition at about 0.1% to about 10%, such as about 0.5% to about 5%, or about 1% to about 3% by weight.

Alditols which may be used in pharmaceutical compositions are well known in the art. Such alditols include, but are not limited to, one or more of the following: mannitol, sorbitol, maltitol, and xylitol. In one embodiment, the alditol is mannitol. Saccharides for use in pharmaceutical compositions are well known in the art. Such saccharides include, but are not limited to, one or more monosaccharides, disaccharides, and oligosaccharides composed of 2-10 monosaccharides. Monosaccharides, also known as reducing sugars, include, but are not limited to, aldoses, hemiacetals, and cyclic hemiacetals. Disaccharides are generally defined as two monosaccharide units joined together by a glycoside linkage. Oligosaccharides are generally defined as carbohydrates that hydrolyze to yield 2 to 10 molecules of a monosaccharide, Monosaccharides, disaccharides, and oligosaccharides include, but are not limited to, sucrose, maltose, cellobiose, lactose, trehalose, glucose, fructose, galactose, ribose, or deoxyribose. In one embodiment, the saccharide is a monosaccharide or a disaccharide. In another embodiment, the saccharide is a disaccharide. In a further embodiment, the saccharide is sucrose.

Exemplary surfactants and surface active agents may be selected from known pharmaceutical excipients such as, for example, gelatin, casein, lecithin, stearic acid or other fatty acids, benzalkonium chloride, calcium stearate, glyceryl monostearate or other fatty acid salts, polyethylene glycols, silicon dioxide, methylcelluloses or carboxymethylcelluloses, sodium stearyl fumarate, magnesium stearate, alginate, or any other surface modifying compounds known in the art. Compounds which function as wetting agents, such as, for example, pharmaceutically acceptable detergents and cetyl alcohols also are contemplated for use.

Examples of lubricants include, but are not limited to, talc, calcium stearate, sodium stearyl fumarate, stearic acid, magnesium stearate, solid polyethylene glycols, and cocoa butter. Examples of binders, fillers, or extenders include, but are not limited to, carrageenan, starches, lactose or other sugars, polyvinylpyrrolidone, sodium citrate, dicalcium phosphate and other alkaline inorganic salts, carboxylmethylcellulose and other cellulose polymers, alginates, gelatins, microcrystalline cellulose, sorbitol, sodium chloride, chitosan, hydrogenated vegetable oil, kaolin, glycerol palmitostearate, magnesium carbonate, and calcium carbonate.

Pharmaceutical compositions may be made according to the following general steps. Those of skill in the art are aware of equivalent methods and variations which produce the same general result. Therefore, the general instructions and the example, which follows, should not be considered to be strictly limiting. A portion or all of the acacia is dissolved in water. Propyl gallate, butylated hydroxyanisol, butylated hydroxytoluene, or any combination thereof is dissolved in alcohol. An alditol such as mannitol, a saccharide such as sucrose, and a granulation aid such as microcrystalline cellulose are screened or passed through a mill. The dry mixture is then blended with the thyroxine ingredient, for example, levothyroxine sodium. The mixture is then granulated by adding the propyl gallate, butylated hydroxyanisol, or butylated hydroxytoluene, and acacia solutions. The granulated mixture is dried, cooled, then passed through a mill. In one embodiment, the acacia and thyroxine are blended together as dry ingredients.

In one embodiment, additional excipients such as microcrystalline cellulose or dicalcium phosphate may also be incorporated into the granulation, but need not be added until the active ingredient is intimately mixed with the alditol and/or the sucrose. Therefore, the microcrystalline cellulose or other diluent functions as a granulation aid and compression enhancer (for tablet or capsule formulations) and not as a specific carrier for the thyroxine active drug.

In one embodiment, the wet granulation is dried, milled, and optionally further blended. The granulation intermediate then may be stored or directly mixed with further ingredients such as excipients to form a composition suitable for compression into tablets, filling into capsules, or dissolved or suspended to form a liquid dosage form.

Without wishing to be bound by theory, it is believed that the stabilizing effect achieved with these formulations is due to the presence of acacia and propyl gallate, butylated hydroxyanisol, butylated hydroxytoluene, or combinations thereof in the final dosage form, and specifically the mixing of acacia and propyl gallate, butylated hydroxyanisol, butylated hydroxytoluene, or combinations thereof with the active ingredient at an early stage of manufacture. In one embodiment, processing of the active ingredient should be conducted at temperatures below about 60° C.

Pharmaceutical compositions may be prepared for administration orally, rectally, vaginally, transmucosally, transdermally, parenterally, subcutaneously, and intramuscularly. Pharmaceutically acceptable excipients which are suitable for use in compositions for these methods of administration are known to those of skill in the art. Generally, excipients contemplated for use in these compositions may include, but are not limited to, adjuvants, preservatives, buffers, fillers, extenders, carriers, binders, diluents, glidants, lubricants, surfactants, wetting agents, surface active agents, suspending agents, and solvents. Compounds such as dyes and colorants, sweeteners, flavorings, perfuming agents, and taste-masking ingredients also may be included in compositions. Any pharmaceutically acceptable excipient, such as ingredients to aid in processing, to improve taste, or to improve appearance are contemplated for use in this composition. In addition, other active ingredients may be included to produce a dual or multiple active ingredient composition.

Examples of solid dosage forms that may be prepared include, but are not limited to, tablets, capsules, rectal or vaginal suppositories, pills, dragees, lozenges, granules, beads, microspheres, pellets, powders, or any combination thereof. Formulations also may be prepared in the form of solutions, suspensions, emulsions, syrups, and elixirs. These liquid dosage forms may include liquid diluents in addition to the solid ingredients discussed above. Such diluents may include, but are not limited to, solvents, solubilizing agents, suspending agents and emulsifiers, water or saline solutions, ethanol and other pharmaceutically acceptable alcohols, ethyl carbonate, ethyl acetate, propylene glycol, dimethyl formamide, pharmaceutically acceptable oils such as cottonseed, corn, olive, castor, and sesame, fatty acid esters of sorbitan, polyoxyethylene sorbitol, and agar-agar. Formulations can be either immediate or modified release.

The composition may be used for any convenient dosage amount of the active ingredient. Generally, the level of the active ingredient may be increased or decreased according to the judgment of the physician, pharmacist, pharmaceutical scientist, or other person of skill in the art. The amount of the remaining non-active ingredients can be adjusted as needed.

After the solid ingredients of the composition are blended, the composition may be compressed into tablets. Alternatively, the composition may be used to fill capsules such as hard gelatin capsules or used to prepare any other convenient solid dosage form. Compositions may be stored in the form of powders, granulates, intermediates, suspensions, or solutions prior to addition of additional desired pharmaceutical excipients for the production of final dosage forms such as tablets or solid-filled capsules, or final liquid dosage forms such as solutions, syrups, suspensions, emulsions and the like.

The pharmaceutical composition comprising thyroxine, acacia, and an antioxidant selected from propyl gallate, butylated hydroxyanisol, butylated hydroxytoluene, or combinations thereof has improved stability. Under accelerated testing conditions of 40° C. at 75% relative humidity, the compositions retained about 95% to about 105% Theoretical Drug Content (TDC) after 6 months. In one embodiment, under accelerated testing conditions, the decrease in potency after 6 months is less than 5% such as less than 4%, less than 3%, or less than 2.5%. In another embodiment, the composition retained about 99% TDC after 6 months. The stability of the pharmaceutical composition may also be tested at room temperature (25° C.) at 60% relative humidity. In one embodiment, under the room temperature testing conditions the composition retained 95% to 105% TDC after 2 years.

While the present disclosure has illustrated by description several embodiments and while the illustrative embodiments have been described in considerable detail, it is not the intention of the applicant to restrict or in any way limit the scope of the appended claims to such detail. Additional advantages and modifications may readily appear to those skilled in the art.

EXAMPLES

Example 1

Levothyroxine 100 µg tablets

The microcrystalline cellulose, mannitol, and sucrose were screened or milled and then blended with levothyroxine sodium for about 6 minutes. Acacia, dissolved in water, and propyl gallate, dissolved in alcohol, were added over about 10 minutes to granulate the mixture. The wet granulation was dried at a temperature below 60° C. until the moisture content was less than about 4%. The dried granulation was sized by passing it through a mill, and then blended with the additional ingredients listed in the table below using conventional mixing equipment.

Levothyroxine 100 µg tablets were prepared using the following ingredients:

| Ingredient | mg/tablet |
| --- | --- |
| Acacia | 1.5 |
| Propyl gallate | 0.015 |
| Mannitol | 32.385 |
| Sucrose | 19.0 |
| Microcrystalline cellulose | 37.0 |
| Levothyroxine sodium | 0.1 |
| Croscarmellose sodium | 7.7 |

-continued

| Ingredient | mg/tablet |
| --- | --- |
| Magnesium stearate | 2.00 |
| Colloidal silicon dioxide | 0.3 |
| Total | 100 mg |

Example 2

Levothyroxine 100 µg with propyl gallate & BHA

Tablets were made according to Example 1, except half the mass of the propyl gallate has been substituted with butylated hydroxyanisol.

Example 3

Levothyroxine 100 µg with BHA

Tablets were made according to Example 1, except all the propyl gallate has been substituted with butylated hydroxyanisol.

Example 4

Stability Testing

Tablets made according to Examples 1 to 3 were stored at 40° C. for 24 weeks at 75% relative humidity. The tablets were then analyzed for drug potency using an HPLC standard assay. The change in potency of the tablets of Example 1 was −2.1%. Evaluation of the potency of Example 1 shows that the new composition yields a product which demonstrates improved stability.

| | Stability testing at 40° C. and 75% relative humidity | | | | | | | | |
| --- | --- | --- | --- | --- | --- | --- | --- | --- | --- |
| Example | Initial Assay | 4 wk Assay | 4 wk Δ | 8 wk Assay | 8 wk Δ | 12 wk Assay | 12 wk Δ | 24 wk Assay | 24 wk Δ |
| 1 | 101.1 | 100.9 | −0.1 | 102.0 | 0.9 | 101.5 | 0.4 | 99.0 | −2.1 |
| 2 | 101.8 | 100.3 | −1.4 | 99.8 | −2.0 | NA | NA | 99.1 | −2.7 |
| 3 | 104.3 | 103.6 | −0.7 | 102.5 | −1.8 | 103.3 | −1.0 | 100.0 | −4.3 |

What is claimed is:

1. A pharmaceutical composition comprising thyroxine, acacia, and about 0.001% wt % to about 0.5% wt % of an antioxidant selected from propyl gallate, butylated hydroxyanisol, and butylated hydroxytoluene, and
   wherein the composition comprises from about 0.1% wt % to about 10% wt % acacia.

2. The composition of claim 1, wherein the composition comprises from about 0.25% wt % to about 2.5% wt % acacia.

3. The composition of claim 1, wherein the composition comprises from about 0.4% wt % to about 2.0% wt % acacia.

4. The composition of claim 1, wherein the composition comprises from about 0.005% wt % to about 0.5% wt % propyl gallate.

5. The composition of claim 4, wherein the composition comprises about 1% wt % to about 2% wt % acacia.

6. The composition of claim 1, wherein the composition comprises from about 0.005% wt % to about 0.5% wt % butylated hydroxyanisol.

7. The composition of claim 1, wherein the composition comprises from about 0.005% wt % to about 0.5% wt % butylated hydroxytoluene.

8. The composition of claim 1, wherein the thyroxine comprises levothyroxine sodium.

9. The composition of claim 8, wherein the composition comprises from about 0.4% wt % to about 2.0% wt % acacia and from about 0.005% wt % to about 0.5% wt % of the antioxidant.

10. The composition of claim 1, wherein the composition is a unit dosage form which comprises about 0.1 µg to about 5000 µg thyroxine.

11. The composition of claim 1, wherein the composition additionally comprises sucrose, microcrystalline cellulose, and mannitol.

12. The composition of claim 11, wherein the composition comprises from about 5% wt % to about 70% wt % sucrose, from about 5% wt % to about 90% wt % microcrystalline cellulose, and from about 5% wt % to about 90% wt % mannitol.

13. The composition of claim 12, wherein the composition is a solid oral dosage form.

14. The composition of claim 1, wherein the decrease in potency, after 6 months at the accelerated conditions of 40° C. and 75% relative humidity, is less than 5%.

15. The composition of claim 14, wherein the decrease in potency, after 6 months at the accelerated conditions of 40° C. and 75% relative humidity, is less than 2.5%.

16. The composition of claim 1, wherein the composition is a solid oral dosage form.

17. The composition of claim 16, wherein the composition is a tablet.

18. The composition of claim 1, wherein the composition comprises about 1.5% wt % acacia.

19. A method for treating thyroid disorders comprising orally administering the composition of claim 1 to a patient in need thereof.

20. The method of claim 19, wherein 25 to 300 µg of thyroxine is administered once daily.

* * * * *